US008896462B2

(12) United States Patent
Skoldengen et al.

(10) Patent No.: US 8,896,462 B2
(45) Date of Patent: Nov. 25, 2014

(54) METHODS FOR LOW POWER COMMUNICATION IN AN IMPLANTABLE MEDICAL DEVICE

(75) Inventors: Niklas Skoldengen, Taby (SE); Hans Abrahamson, Stockholm (SE); Therese Danielsson, Uppsala (SE)

(73) Assignee: St. Jude Medical AB, Jarfalla (SE)

( * ) Notice: Subject to any disclaimer, the term of this patent is extended or adjusted under 35 U.S.C. 154(b) by 368 days.

(21) Appl. No.: 13/509,864

(22) PCT Filed: Nov. 27, 2009

(86) PCT No.: PCT/EP2009/065992
§ 371 (c)(1),
(2), (4) Date: May 15, 2012

(87) PCT Pub. No.: WO2011/063848
PCT Pub. Date: Jun. 3, 2011

(65) Prior Publication Data
US 2012/0229299 A1    Sep. 13, 2012

(51) Int. Cl.
*G08C 15/06* (2006.01)
*A61N 1/372* (2006.01)
*A61N 1/37* (2006.01)

(52) U.S. Cl.
CPC ........... *A61N 1/37276* (2013.01); *A61N 1/3718* (2013.01)
USPC ................ 340/870.02; 340/870.07; 340/10.1; 340/10.6; 600/374; 600/481; 600/485; 600/508; 607/31; 607/32; 607/60

(58) Field of Classification Search
CPC ......................... A61N 1/37276; A61N 1/3718
USPC .................... 340/870.02, 870.06, 10.1, 10.6; 600/374, 481, 485, 508; 607/31, 32, 60
See application file for complete search history.

(56) References Cited

U.S. PATENT DOCUMENTS

| 6,719,701 | B2 * | 4/2004 | Lade ............................. 600/485 |
| 8,391,980 | B2 * | 3/2013 | Bornzin et al. ................. 607/27 |
| 2003/0083570 | A1 | 5/2003 | Cho et al. |
| 2005/0245971 | A1 | 11/2005 | Brockway et al. |
| 2007/0167996 | A1 | 7/2007 | Dudding et al. |

OTHER PUBLICATIONS

International Preliminary Report on Patentability—Int'l App. No. PCT/EP2009/065992; Int'l Filing Date: Nov. 27, 2009.
International Search Report—Int'l App. No. PCT/EP2009/065992; Int'l Filing Date: Nov. 27, 2009.

* cited by examiner

*Primary Examiner* — Tai T Nguyen

(57) ABSTRACT

The present invention is directed to an implantable medical device and a method for power management for power efficient use of RF telemetry during, for example, conditions where long periods of continuous monitoring of the device and the patient is desired such as during MRI procedures. A protocol module adapted to, at receipt of a low power protocol indication, activate and use a low power protocol for communication between the device and external units. The protocol module is capable of switching between different communication protocols including a low power communication protocol and a default RF communication protocol depending on, for example, whether continuous long-term monitoring of the patient is performed. During the low power communication protocol, the protocol module is adapted to select parts of stored electrophysical and/or hemodynamical signal waveforms for telemetric transmission and to create communication packages having a predetermined length using the selected parts of the electrophysiological and/or hemodynamical signal waveform. Further, a transmitter is instructed to transmit the communication packages at predetermined transmission intervals and the telemetry module is instructed to power down the transmitter or set the transmitter in a lowest possible activation state during intermediate periods between the transmission intervals.

16 Claims, 4 Drawing Sheets

METHODS FOR LOW POWER COMMUNICATION IN AN IMPLANTABLE MEDICAL DEVICE

TECHNICAL FIELD

The present invention generally relates to implantable medical devices, such as pacemakers, implantable cardiac monitors, and implantable cardioverters/defibrillators (ICDs). In particular, the present invention relates to implantable medical devices including telemetric capabilities and methods for telemetric communication in such devices.

BACKGROUND OF THE INVENTION

Implantable medical devices (IMDs) such as pacemakers and implantable cardioverters/defibrillators (ICDs) typically have a non-rechargeable battery with an expected lifetime of 3-15 years, with 5-10 years being most common. This has been made possible with advancements in battery and capacitor technology, as well as reducing power requirements of the components within the device. At the same time, many more features, therapies and capabilities are provided in modern IMDs that simply require additional power.

Therefore, with these considerations in mind, power management is an important aspect in the design and manufacture of IMDs.

During recent years distance telemetry capabilities have been included in most IMDs, wherein the IMD communicates with an external device via radio frequency communication. This permits communication with the IMD without requiring presence of a programming head in the proximity of the patient during the communication session. In-office follow-ups are easier and less cumbersome. Further, this also permits a patient's IMD to communicate in virtually any environment without encumbering the patient. For example, a patient may be provided with a home monitor that communicates with the IMD via RF communication and transmits the data to a central server. Thereby, it is, for example, possible to perform long-term monitoring of the cardiac status of the patient.

While providing many benefits, distance telemetry also utilizes scarce power resources, especially during long-term monitoring sessions and there is a need within the art of power management for efficient use of RF telemetry.

Another situation where these scarce power resources may be over exploited leading to severe depletion or drain of the battery may occur during MRI (Magnetic Resonance Imaging) procedures since it is desired to be able to supervise or monitor the patient, e.g. the cardiac status, as well as the functionality of the IMD during such procedures. In theory, the battery may be essentially drained if the patient is monitored during an extensive MRI procedure. MRI is an effective, non-invasive magnetic imaging technique for generating sharp images of the internal anatomy of the human body, which provides efficient means for diagnosing disorders such as neurological and cardiac abnormalities and for spotting tumours and the like. Briefly, the patient is placed within a centre of a large superconducting magnet that generates a powerful static magnetic field. The static magnetic field causes protons within tissues of the body to align with an axis of the static field. A pulsed radio frequency (RF) magnetic field is then applied causing the protons to begin to precess around the axis of the static field. Pulsed gradient magnetic fields are then applied to cause the protons within selected locations of the body to emit RF signal, which are detected by sensors of the MRI system. Based on the RF signals by the protons, the MRI system then generates a precise image of the selected locations of the body, typically image slices of organs of interest.

Pacemakers and ICDs typically include sensing and detecting circuits for sensing or detecting electrophysiological signal of the heart which signal are used, for example, in the pacing of the patient and/or for monitoring a cardiac status of the patient. As mentioned above, it would be preferable to allow medical devices such as pacemakers or ICDs implanted within the patient to continue to operate in its normal modes during an MRI procedure as long as heating criteria is met, arrhythmias are not induced, unnecessary pacing pulses or shocks are not delivered, and any necessary therapy is not improperly inhibited. That is, it would be desirable to allow the device to continue to monitor the heart of the patient for arrhythmias or other medical conditions even during an MRI procedure. It is also desirable to control the device to transmit monitoring and diagnostic information during the MRI procedure to an external monitoring and control system so that medical personnel can monitor the status of the implanted device and the health of the patient during the MRI scan procedure. In particular, it is of interest to monitor the IEGM of the patient during an MRI scan procedure at the external monitoring and control system to allow the medical personnel to monitor the cardiac status and health of the patient.

An MRI scan procedure normally takes up to two hours and monitoring the cardiac status and health of the patient as well as the functionality of the device thus requires that the RF communication circuits of the device is active and transmits IEGM data during a long period of time. This puts a heavy load on the battery and processing circuits of the device. For example, such long transmission periods draw high currents which deplete the battery and may in fact even damage the battery.

To conclude, power management is a very important aspect in the design and manufacture of IMDs and, in particular, power management for efficient use of RF telemetry during long-term monitoring of the patient, e.g. during MRI procedures, since it uses scarce power resource.

SUMMARY OF THE INVENTION

The present invention provides an improved medical device and method that are capable of fulfilling at least some of the above-mentioned needs or provide a solution to or alleviating at least some of the above-mentioned problems in the prior art.

A particular object of the present invention is to provide an implantable medical device and a method for power management for power efficient use of RF telemetry during, for example, conditions where long periods of continuous monitoring of the device and the patient is desired such as during MRI procedures.

This and other objects of the present invention are achieved by means of a method and an implantable medical device having the features defined in the independent claims. Different embodiments of the invention are characterized by the dependent claims.

According to an aspect of the present invention, there is provided an implantable medical device comprising a telemetry module with a transmitter and a receiver. An input module is connectable to at least one electrode. The input module is adapted to obtain electrophysiological and/or hemodynamical signals from the heart via the at least one electrode at a predetermined sampling frequency. The medical device further comprises a storage unit for storage of the obtained electrophysiological and/or hemodynamical signals and a protocol module adapted to, at receipt of a low power protocol indication, activate and use a low power protocol for communication between the device and external units. The protocol module is capable of switching between different communication protocols including a low power communication protocol and a default RF communication protocol depending on, for example, whether continuous long-term monitoring of the patient is performed. During the low power communication protocol, the protocol module is adapted to select parts of stored electrophysical and/or hemodynamical signal waveforms for telemetric transmission and to create communication packages having a predetermined length using the selected parts of the electrophysiological and/or hemodynamical signal waveform. Further, the transmitter is instructed to transmit the communication packages at predetermined transmission intervals and the telemetry module is instructed to power down the transmitter or set the transmitter in a lowest possible activation state during intermediate periods between the transmission intervals.

According to a second aspect of the present invention, there is provided a method for an implantable medical device comprising a telemetry module with a transmitter and a receiver. An input module is connectable to at least one electrode, the input module being adapted to obtain electrophysiological and/or hemodynamical signals from the heart via the at least one electrode at a predetermined sampling frequency. The method comprises storing of the obtained electrophysiological and/or hemodynamical signals and, at receipt of low power protocol indication, activating and using a low power protocol for communication between the device and external units, which includes selecting parts of stored electrophysical and/or hemodynamical signal waveforms for telemetric transmission and creating communication packages having a predetermined length using the selected parts of the electrophysiological and/or hemodynamical signal waveform. Further, the method includes instructing the transmitter to transmit the communication packages at predetermined transmission intervals, and instructing the telemetry module to power down the transmitter or set the transmitter in a lowest possible activation state during intermediate periods between the transmission intervals.

Preferably, the present invention is implemented in a pacemaker, an implantable monitor, or implantable cardioverter/defibrillator (ICDs). Heart stimulator such as pacemakers, dual chamber stimulators and implantable cardioverter/defibrillator (ICDs) can be set in electrical contact with the heart via medical leads implanted within the heart or at the heart provided with electrodes. The medical leads can be connected to the stimulator to electrically connect the stimulator to cardiac tissue. Implantable cardiac monitors are provided with electrodes on the cap or outer surface, which enables the implantable monitor to monitor, for example, the cardiac rhythm without the use of medical leads implanted within or at the heart. An implantable cardiac monitor may be used to diagnose syncope, which is a common and disabling condition that is associated with an increased risk of morbidity and mortality. One suitable cardiac monitor in which the present invention may be implemented is sold under the name SJM Confirm® Implantable Cardiac Monitor and manufactured by St. Jude Medical Inc.

Thus, the present invention is based on the idea of providing an implantable medical device and method having the capability of switching between different communication protocols or communication modes depending of, for example, the environmental conditions or monitoring requirements in order to obtain a more efficient power management and, in particular, in order to reduce the current drain of the battery. In particular, a low power protocol is designed for use long-term monitoring sessions, such as during MRI scan procedures, taking into consideration specific conditions prevailing during long-term monitoring sessions. The low power protocol according to the present invention entails an efficient use of the available battery capacity in that the average current drain use can be significantly reduced in comparison a normal RF communication. This is achieved by transmitting small or short IEGM data communication packages with a predetermined delay or during predetermined transmission intervals. The IEGM signals are obtained at a reduced sampling frequency or the IEGM signals are obtained at a normal sampling frequency but selected parts of the IEGM signals are transmitted and thereby makes it possible to form small or short IEGM data communication packages. The transmitter is powered down or is set in an inactive state during the intermediate periods between the transmission intervals and is only woke up and activated at each transmission interval. In total, this low power protocol provides a significantly reduced average current drain and load on the battery. The low power protocol according to the present invention therefore allows very long RF communication sessions as required during, for example, MRI scan procedures.

Furthermore, the low power protocol according to the present invention enables a supervision of the patient in a safe and power efficient way as well as a supervision of device implant functionality during a MRI scan via display of, for example, IEGM in real time (however, with a delay equal to the intermediate period, e.g. 3, 4 or 5 seconds) on the programmer. The medical personnel supervising the patient on the programmer will experience the display of IEGM data as a real time display since the transmitted IEGM data is continuously transmitted at the predetermined transmission intervals.

Preferably, the low power protocol is used during presence of MRI fields or other conditions when a monitoring of the patient and/or a monitoring of the functionality of the device is required during long period of times. During normal conditions a RF default protocol can be used. However, the power efficient low power protocol may also be used during monitoring sessions of the patient in other situations, for example, in home monitoring situations or at distance monitoring situations where it is of interest to continuously monitor the patient during long periods of time.

According to an embodiment of the present invention, the sampling frequency of the measurements of the electrophysiological and/or hemodynamical signals is reduced when the low power protocol is activated or initiated. The selected parts of the electrophysiological and/or hemodynamical signals correspond to the stored electrophysiological signals. Alternatively, parts of stored electrophysiological and/or hemodynamical signal waveforms are selected, wherein the parts are selected with predetermined intermediate time periods.

In an embodiment of the present invention, a low power protocol indication is received from an external unit via the telemetry module, which indication prompt a switch to the low power protocol. This indication may be sent manually by a physician or automatically by an external device at the initiation of a long-term session of continuous monitoring of the status of the patient and/or of the functionality of the device. This long term monitoring may be performed in connection with an MRI scan procedure. For example, a RF telemetry antenna of an external monitoring system may be adapted to periodically emit MRI indicating signals to notify the IMD of the presence of an MRI field. Thereby, the IMD is capable of detecting entry of the patient into a MRI procedure room. The MRI indicating signal may also be sent manually by the medical personnel being present in the MRI procedure room using the external monitoring system.

In an exemplary embodiment of the present invention, an MRI field detector is adapted to detect a presence of an external magnetic field having a magnetic field strength above a predetermined threshold as a MRI field and to indicate whether a MRI field is present, and to provide the indication of the presence of a MRI field to the protocol module. In a specific implementation, the MRI field detector is a Hall Effect sensor. Additionally and/or alternatively other types of sensors capable of detecting other properties of the electromagnetic fields that may be produced during the MRI scan procedure may be used in the detector to detect the presence of the high static magnetic field. For example, other fields associated with the MRI scan procedure, such as a static gradient magnetic field, a variable gradient magnetic field, radio-frequency pulses, or a variable magnetic field may be detected by the detector.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

BRIEF DESCRIPTION OF THE DRAWINGS

Exemplifying embodiments of the invention will be described below with reference to the accompanying drawings, in which.

DESCRIPTION OF EXEMPLIFYING EMBODIMENTS

The following is a description of exemplifying embodiments in accordance with the present invention. This description is not to be taken in limiting sense, but is made merely for the purposes of describing the general principles of the invention. It is to be understood that other embodiments may be utilized and structural and logical changes may be made without departing from the scope of the present invention. Thus, even though particular types of implantable medical devices such as heart stimulators will be described, e.g. biventricular pacemakers, the invention is also applicable to other types of cardiac stimulators such as dual chamber stimulators, implantable cardioverter defibrillators (ICDs), implantable monitors etc. Heart stimulator such as pacemakers, dual chamber stimulators and implantable cardioverter/defibrillator (ICDs) can be set in electrical contact with the heart via medical leads implanted within the heart or at the heart provided with electrodes. The medical leads can be connected to the stimulator to electrically connect the stimulator to cardiac tissue. Implantable cardiac monitors are provided with electrodes on the cap or outer surface, which enables the implantable monitor to monitor, for example, the cardiac rhythm without the use of medical leads implanted within or at the heart. An implantable cardiac monitor may be used to diagnose syncope, which is a common and disabling condition that is associated with an increased risk of morbidity and mortality. One suitable cardiac monitor in which the present invention may be implemented is sold under the name SJM Confirm® Implantable Cardiac Monitor and manufactured by St. Jude Medical Inc.

The present invention efficiently and significantly reduces the drain of the battery during continuous long-term monitoring of a patient and/or functionality of an IMD via RF communication and provides effective power management during such long-term data transfer sessions including, for example, long-term monitoring of the patient at home or during MRI scan procedures.

Below, the present invention will be discussed in a specific context where power management and efficient use of the battery capacity is crucial to avoid a severe or complete drain of the battery or even damage of the battery.

Figure 1:
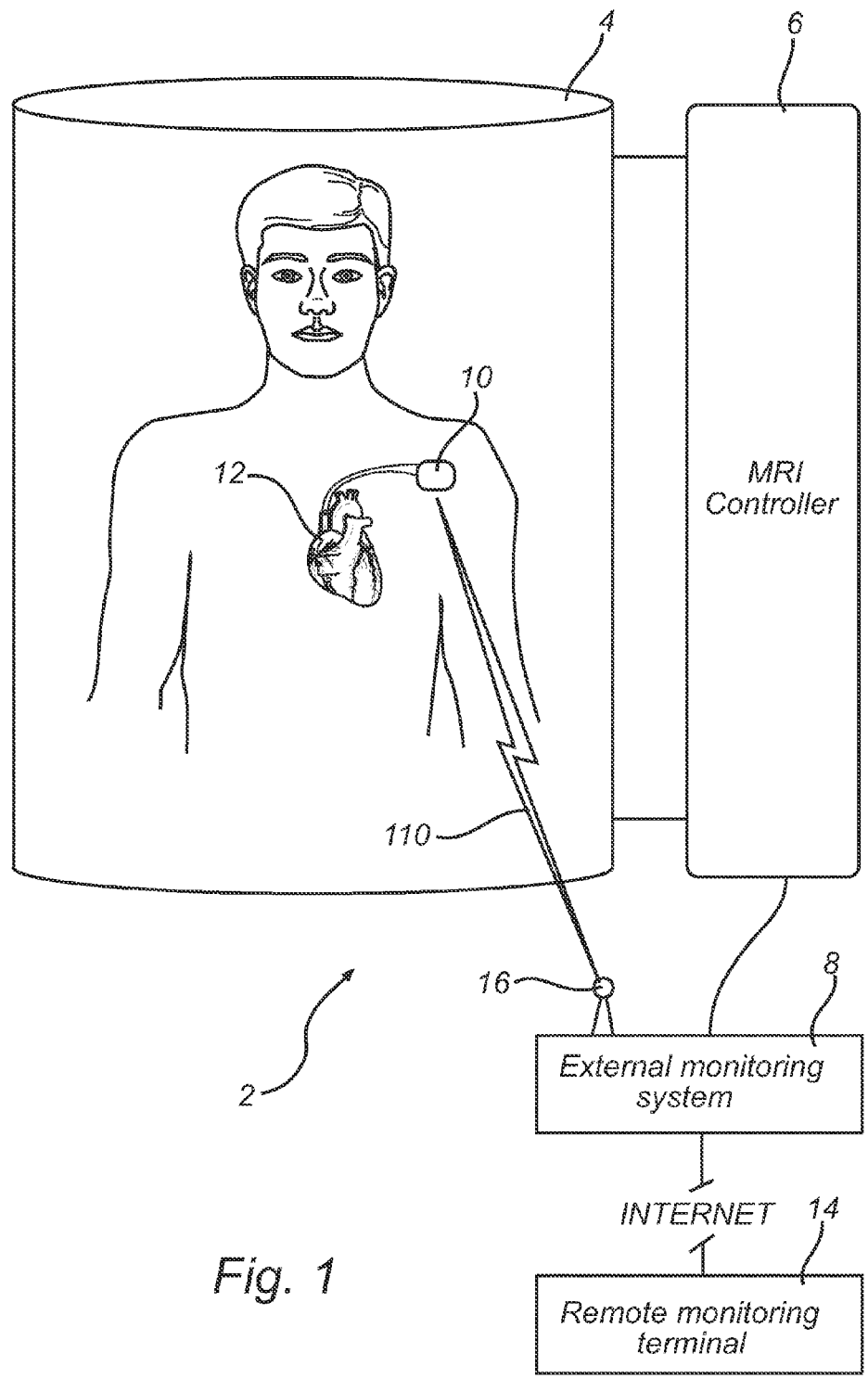
FIG. 1 is a representation of an MRI system along with a patient with a pacer/ICD implanted therein that is capable of communicating with an external monitoring system during an MRI procedure.
Figure 2:
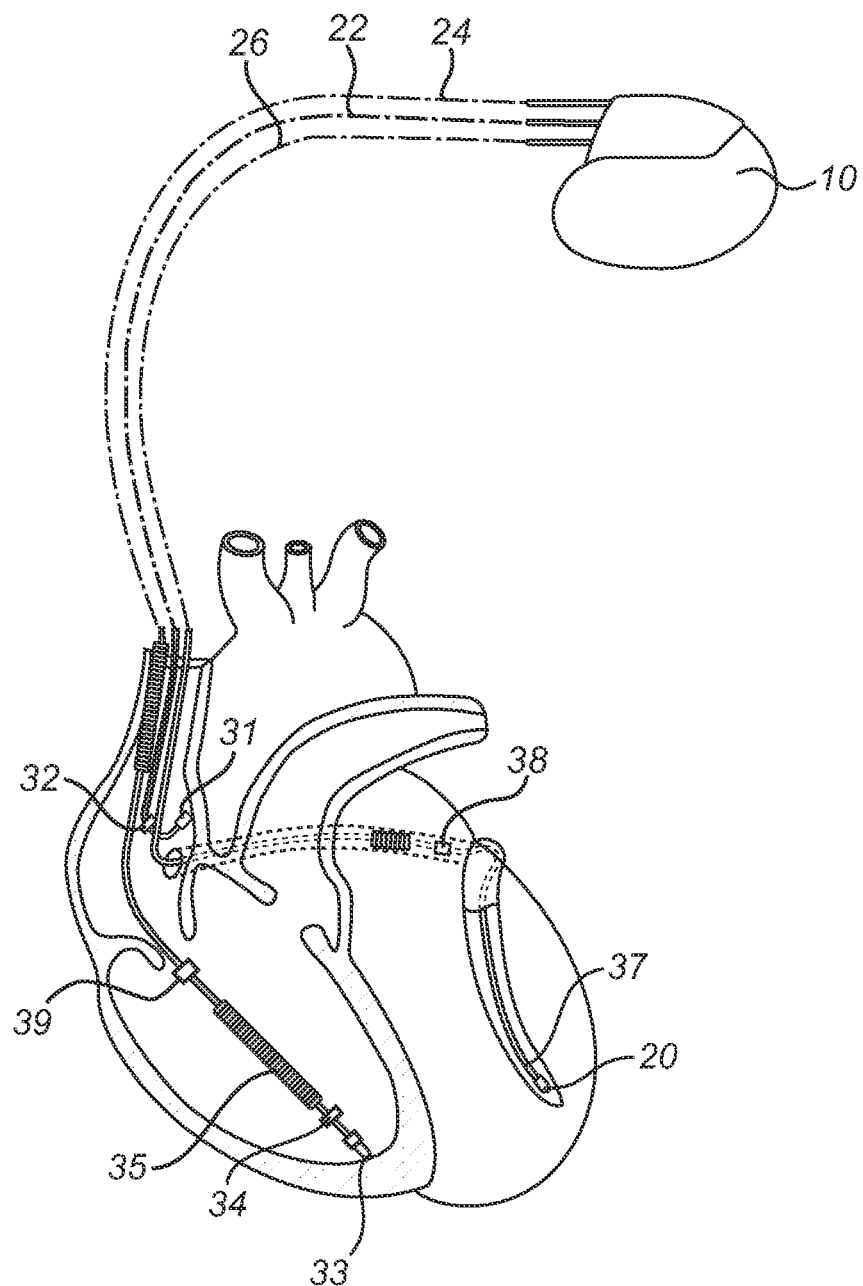
FIG. 2 is a simplified, partly cutaway view, illustrating an implantable medical device according to the present invention with a set of leads implanted into the heart of a patient.
Figure 3:
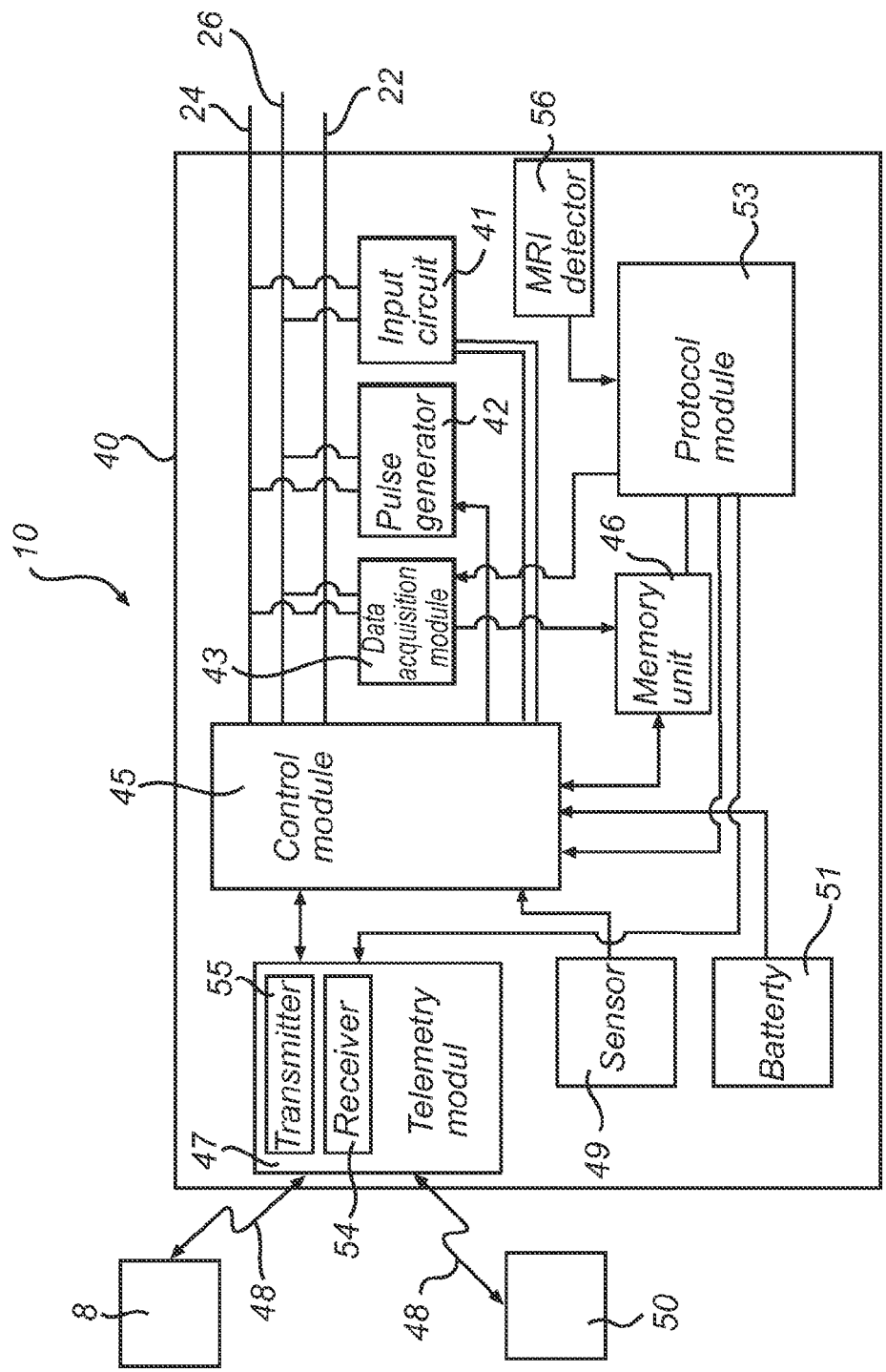
FIG. 3 is a functional block diagram form of the implantable medical device shown in FIGS. 1 and 2, illustrating basic circuit elements that provide, for example, pacing stimulation in the heart and for acquiring simultaneous impedance signals from several electrode configurations according to the present invention.

FIG. 1 illustrates an overall MRI system 2 including an MRI machine 4 adapted to generate MRI fields during an MRI procedure for examining a patient. The MRI machine 4 operates under the control of an MRI controller 6, which controls the strength and orientation of the fields generated by the MRI machine 4 and derived images of portions of the patient therefrom, in accordance with otherwise conventional techniques. MRI machines and imaging techniques are well known and will not be described in detail herein. An external monitoring system 8 is also provided that communicates via long range RF telemetry during the MRI procedure with an implantable medical device (IMD) 10, e.g. a pacer/ICD, implanted within the patient to receive transmissions of electrophysiological signals and/or hemodynamical signals sensed within the patient by the IMD 10 during the MRI procedure, as well as other diagnostic data to be described in greater detail below. A lead system 12 is coupled to the IMD 10 for sensing the electrophysiological signals within the heart of the patient, such as atrial IEGM signals and ventricular IEGM signals, and for delivering any needed pacing pulses or shock therapy. In FIG. 1 only two leads are shown, but, more than two leads are of course also conceivable, e.g. three or four leads. A more compete lead system is illustrated in FIGS. 2 and 3 and described below. In general, any of the electrophysiological signals sensed using the pacing/sensing leads might potentially be transmitted to the external monitoring system 8 during the MRI procedure for display thereon.

The lead system 12 may also include various physiological sensors (not separately shown in FIG. 1) for sensing hemodynamic signals or other signals within the patient, such as sensors operative to sense intracardiac pressure, blood oxygen saturation (i.e. blood $SO_2$), blood temperature, and PPG signal etc. In some cases, the sensors may be implanted elsewhere in the patient or may be mounted in or on the IMD 10. Any of the various hemodynamic signals or other signals sensed using the sensors might potentially be transmitted to the external monitoring system 8 during the MRI procedure of display thereon. Furthermore, during the MRI procedure, the IMD 10 may analyze the various sensed signals to detect abnormal conditions such as tachyarrythmias, sudden drops in blood pressure, sudden changes in blood temperature etc. Warning signals pertaining to such abnormal conditions may also be transmitted from the IMD 10 to the external monitoring system 8 during the MRI procedure for review.

The external monitoring system 8 may be adapted to analyze any of the various signals received from the IMD 10 to detect abnormal conditions, including abnormal electrode tip temperatures, abnormal induced current levels, tachyarrythmias etc. to generate suitable warning signal for the attending personnel and to deactivate the MRI machine 4, if appropriate. The IMD 10 may be adapted to transmit warnings and other information pertaining e.g. to electrode tip temperatures or induced currents to the external monitoring system 8. The external monitoring system 8 may be provided with more sophisticated software or hardware than included within the IMD itself, for use in analyzing the IEGM signals and cardiac pressure signals and the like to, for example, detect abnormal conditions. In this regard, the external monitoring system 8 may be provided with software requiring more extensive memory capacity or processing resources than available within the IMD 10. Furthermore, information received or generated by the external monitoring system 8 may be forwarded via internet or other appropriate communications networks to a remote monitoring terminal 14 for review thereon.

To permit communication with the IMD 10, for example, during the MRI procedure, the external monitoring system 8 includes an RF telemetry antenna 16 adapted to communicate via MICS (Medical Implant Communications Service) or ISM (industrial, scientific and medical) channels with a RF telemetry module within the IMD 10 (shown in FIGS. 2 and 3 and discussed below). MICS band frequencies are in the range of 402 MHz-405 MHz and ISM band frequencies are in the range of 2.5 GHz-5.0 GHz.

The IMD 10 comprises (as will be discussed below with reference to FIG. 3) a protocol module adapted to switch to a low power protocol at receipt of signal indicating the low power protocol should be activated, for example, in connection with a long-term monitoring session. The indication or signal may be sent manually from the remote monitoring terminal 14 or the external monitoring system 8.

The indication may indicate the presence of an MRI field. For that purpose, the RF telemetry antenna 16 of the external monitoring system 8 may be adapted to periodically emit MRI indicating signals to notify an IMD 10 of the presence of an MRI field. Thus, the IMD 10 is capable of detecting entry of the patient into a MRI procedure room. The MRI indicating signal may also be sent manually by the medical personnel being present in the MRI procedure room using the external monitoring system 8. Moreover, as will be described below, the IMD 10 may include an MRI interference signal detector, for example, a Hall Effect sensor, thereby enabling the IMD to detect the presence of an MRI field.

Upon detection or notification of an MRI field, the IMD 10 is adapted to switch from a default RF communication mode or protocol to an MRI communication mode or protocol (as will be discussed below) for use in the presence of the MRI fields.

With reference now to FIGS. 2 and 3, an exemplary IMD according to the present invention will be discussed. In FIG. 2, a simplified diagram of the IMD 10 which in this embodiment is a dual-chamber stimulation device.

To provide atrial chamber pacing stimulation and sensing, the IMD 10 is arranged for electrical communication with a heart 20 by way of left atrial lead 22 having an atrial tip electrode 31 and an atrial ring electrode 32 implanted in the atrial appendage. The IMD 10 is further in electrical communication with the heart 20 by way of a right ventricular lead 24 having, in this embodiment, a ventricular tip electrode 33, a right ventricular ring electrode 34, and a right ventricular coil electrode 35. The ventricular lead 24 is thus capable of receiving cardiac signals and delivering stimulation in the form of pacing and shock therapy to the right ventricle. To sense left atrial and ventricular cardiac signals and to provide left chamber pacing therapy, the IMD 10 is coupled to coronary sinus lead 26 designed for placement in the coronary sinus such that a distal electrode is positioned adjacent to the left ventricle and/or additional electrodes adjacent to the left atrium. The coronary sinus lead 26 includes, in this embodiment, a left ventricular tip electrode 37 and a left atrial ring electrode 38. With this configuration, biventricular pacing can be performed. Although only three leads are shown in FIG. 2, it should also be understood that additional stimulation leads (with one more pacing, sensing, and/or shocking electrodes) may be used in order to efficiently and effectively provide pacing stimulation to the left and/or right side of the heart or atrial cardioversion and/or defibrillation.

Additionally, a hemodynamic sensor 39 is mounted to the right ventricle lead 24 adapted to transmit one or more hemodynamical signal, such right ventricular pressure signals. Numerous other sensors can be mounted to the various pacing/sensing leads or to other leads.

A simplified block diagram of the internal components of the IMD 10 is shown in FIG. 3. While a particular IMD is shown, for illustrative purposes only, one of skill in the art could readily duplicate, eliminate or disable the appropriate circuitry in desired combinations.

According to this embodiment, the IMD 10 is a pacemaker having a microprocessor based architecture. The housing 40 of the IMD 10, shown schematically in FIG. 3, is often referred to as the "can", "case", or "case electrode" and may be programmably selected to act as the return electrode in, for example, "unipolar" modes. The housing 40 further includes a connector (not shown) having a plurality of terminals (not shown) for connection to the medial leads 22, 24, and 26 and the included electrodes 31, 32, 33, 34, 35, 37, 38, and 39. Thus, the leads 22, 24, and 26 are connectable to the IMD 8 and comprises, as have been illustrated in FIG. 2, one or more electrodes, such a coils, tip electrodes or ring electrodes. These electrodes are arranged to, inter alia, transmit pacing pulses for causing depolarization of cardiac tissue adjacent to the electrode(-s) generated by a pace pulse generator 42 under influence of a control module or microcontroller 45. The rate of the heart 20 is controlled by software-implemented algorithms stored within a microcomputer circuit of the control module 45. As well known in the art, the microcomputer (also referred to as a microprocessor) of the control module is designed specifically for controlling the delivery of stimulation therapy and may further comprise random access memory (RAM) and read-only memory (ROM), logic and timing circuitry, state machine circuitry, and I/O circuitry. Typically, the control module 45 includes the ability to process or monitor input signals (data) as controlled by a program code stored in a designated block of memory. The details of design and operation of the control module 45 are not critical to the invention. Rather, any suitable control module 45 may be used that carries out the functions described herein. The use of microprocessor-based control circuits for performing timing and data analysis functions are well known in the art.

The pulse generator 42 includes an atrial pulse generator (not shown) and a ventricular pulse generator (not shown) adapted to generate pacing stimulation pulses for delivery by the right atrial lead 22, the right ventricular lead 24, and/or the coronary sinus lead 26 via an electrode configuration switch (not shown). The pulse generator 42 is controlled by the control module 45 via appropriate control signals to trigger or inhibit the stimulation pulses.

The control module 45 further includes timing control circuitry (not separately shown) used to control the timing of such stimulation pulses (e.g. pacing rate, atrio-ventricular (AV) delay, atrial interconduction (A-A) delay, or ventricular interconduction (V-V) delay etc.) as well as to keep track of the timing of refractory periods, blanking intervals, noise reduction windows, evoked response windows, alter intervals, marker channel timing, etc., which is well known in the art.

An input circuit 41 selectively coupled to the medical leads 22, 24, and 26 includes atrial sensing circuits (not shown) and ventricular sensing circuits (not shown) for detecting the presence of cardiac activity in each of the four chambers of the heart. The sensing circuits may include sense amplifiers with programmable gain and/or automatic gain control, bandpass filtering, and a threshold detection circuit, as known in the art, to selectively sense cardiac signals. The outputs of the input circuit 41 are connected to the control module 45 which, in turn, is able to trigger or inhibit the pulse generator 42 in a demand fashion in response to the absence or presence of cardiac activity in the appropriate chamber of the heart. Further, the IMD 10 may use the sensing circuits of the input circuit 41 to sense cardiac signals to determine whether a rhythm is physiologic or pathologic in arrhythmia detection purposes.

A data acquisition module 43 including analog-to-digital converters is adapted to acquire analog intracardiac electrogram signals and convert the acquired analog signals to digital signals and store the signals for later processing and/or telemetric transmission to external devices 50 and 8 in a memory unit 46. The data acquisition module 43 is coupled to the medical leads 22, 24, and 26 to sample cardiac across any pair of desired electrodes.

The control module 45 is also connected to the memory unit 46 via a suitable data/address bus (not shown), wherein operating parameters used by the control module 45 can be stored and modified as required, in order to customize the operation of the IMD 10 to suit the needs of a particular patient. Such operating parameters define, for example, pacing pulse amplitude or magnitude, pulse duration, electrode polarity, rate, sensitivity, automatic features, and arrhythmia detection criteria. Other parameters may include base rate, rest rate, and circadian base rate.

The operating parameters of the IMD 10 may be non-invasively programmed into the memory unit 46 through a communication module or telemetry module 47 comprising a receiver 54 and a transmitter 55 in telemetric communication with an external device 50 such as a programmer, or the external monitoring system 8. The telemetry module 46 allows IEGMs and other physiological signal and/or hemodynamic signals as well as, for example, status information related to the operation of the IMD 10 to be sent to the external programmer 50 and/or the external monitoring system 8 through an established communication links 48. To facilitate communication with the external monitoring system 8 and/or the external programmer MICs band components (not shown) and ISM band components (not shown) are provided within the telemetry module 47.

The IMD 10 may further include an activity sensor or other physiologic sensors 49, which may be used to adjust pacing stimulation rate according to the exercise state of the patient. However, the sensor 49 may further be used to detect changes in cardiac output or changes in physiological condition of the heart. While shown as being included within the IMD 10, it is to be understood that the sensor 49 may also be external to the IMD, yet still be implanted within or carried by the patient. A common type of activity sensor is an accelerometer or a piezoelectric crystal mounted within the housing 40. Other types of physiological sensors are also known, for example, sensors that sense the oxygen content of the blood, respiration rate and/or minute ventilation, pH of blood etc.

The IMD 10 additionally includes a battery 51, which provide operating power to all the circuits shown in FIG. 3. The battery 51 may vary depending on the capabilities of the IMD 10. If the system provides low voltage therapy, a lithium iodine or lithium copper fluoride cell may be utilized. If the device provides remote telemetry and sensing and where milliampere-level (up to 300 mA) pulse currents are required to deliver therapy a suitable battery is a battery of the type QMR 2570 manufactured by Greatbatch Medical Inc.

Furthermore, the IMD 10 may also include impedance measuring circuits (not shown) for measuring, for example, thoracic impedance or intra-cardiac impedance.

A protocol module 53 is further included in the IMD 10 adapted to activate and use a low power protocol at receipt of a low power protocol activation signal or indication. This signal or indication may be sent manually, for example, by a physician from the remote monitoring terminal 11 in connection with a long-term monitoring session where the status of the patient and/or the functionality of the device will be monitored continuously over long periods of time at home, which using the normal RF communication protocol may drain the battery partly or completely. The indication may also be an indication of a presence of an MRI field. As discussed above, this indication or signal may be received from external equipment such as the external monitoring system 8, which signal or indication may be sent automatically or manually. By entering into or by activating the power efficient low power protocol, a remote monitoring of the patient as well as over the functionality of the device during the long MRI scan procedure is enabled without risking the health of the battery.

The protocol module 53 is adapted to use a RF default communication protocol during normal conditions, i.e. conditions where it is not necessary to continuously monitor the patient during long periods of time. Thus, at receipt of a default RF communication protocol activation signal, the protocol module 53 may switch from the low power communication mode (where the low power communication protocol is used) to, for example, a RF default communication mode.

As will be explained in more detail below, the protocol module 53 is adapted to instruct the telemetry (or communication) module 47 to power down the transmitter 55 during periods between transmission intervals or sessions when being in the MRI communication mode. At each transmission session, the transmitter 55 is woke up and activated for transmission. Preferably, the transmitter 55 is activated every $3^{rd}$, $4^{th}$, or $5^{th}$ second for transmission of buffered IEGM data.

The IMD 10 may further include a MRI field detector 55 adapted to detect a MRI interference signal. In a preferred embodiment, the detector 55 is a Hall Effect sensor adapted to detect the high static field associated with a MRI scan procedure. The Hall Effect sensor may be capable of detecting magnetic fields having magnetic field strengths in the range of about 0.15 Tesla (1500 Gauss) to about 10 Tesla (100,000 Gauss). Magnetic fields having a magnetic field strength above a threshold of about 0.12 (1200 Gauss) may be an indication of a MRI scan procedure. Additionally and/or alternatively other types of sensors capable of detecting other properties of the electromagnetic fields that may be produced during the MRI scan procedure may be used in the detector 56 to detect the presence of the high static magnetic field. For example, other fields associated with the MRI scan procedure, such as a static gradient magnetic field, a variable gradient magnetic field with a frequency of up to about 5 kHz, radio-frequency pulses with a frequency of up to about 50 MHz, or a variable magnetic field with a frequency of about 64 MHz may be detected by the detector 56.

According to a preferred embodiment of the present invention, the Low power protocol includes buffering the obtained IEGMs, packaging the buffered IEGMs and transmitting the buffered IEGM to the external monitoring system 8 and/or the external programmer 50 in burst with predetermined intervals, for example, every $3^{rd}$, $4^{th}$, or $5^{th}$ second. For the medical personnel viewing the IEGM data on a display of the external monitoring system 8 and/or the programmer 50, the IEGM waveform provide all necessary information but with a delay corresponding to the predetermined interval. Preferably, the communication channel between the implantable medical device and the external device (e.g. the system 8 or the programmer 50) is maintained during the intermediate periods between the regular transmission intervals. The length of the IEGM packages can be made short, for example, about 25 ms due to the fact that only selected parts of the electrophysiological signal of the heart actually are sent. During normal operation, the electrophysiological signal is obtained by the data acquisition module 43 by a sampling frequency of 128 Hz or 256 Hz. According to an embodiment of the invention, only selected samples of the stored IEGM signals are transmitted, for example, every $4^{th}$ sample, which will correspond to sampling frequency of 32 Hz or 64 Hz. In another embodiment, the data acquisition module 43 is instructed to reduce the sampling frequency during the Low power protocol. For example, the electrophysiological signals may be sampled with a frequency of 32 Hz or 64 Hz.

Using the present invention, the load on the battery is significantly reduced in comparison with the load on battery during normal RF communication. In a specific example, using 25 ms packages and information bursts every $3^{rd}$ second, the current consumption is about 0.1 mA and the energy consumption of the battery during an MRI scan procedure (about 3 hours long) is about 0.028% of the total battery capacity. If a normal RF communication protocol would be used during the MRI scan, the current consumption would be 2.8 mA and 0.76% of the battery capacity would be used.

Preferably, the transmitter 55 of the telemetry module 47 is only activated during the transmission sessions, for example, every $3^{rd}$ second. In one embodiment, the transmitter is inactive (i.e. powered down) during the intermediate periods while the control logic and the receiver 54 are active. That is, the transmitter is powered down or is placed in the lowest possible operative capacity. In an alternative embodiment, also the control logic and receiver 54 are powered down during the intermediate period between the transmission bursts. When a transmission bursts or transmission session has been terminated, the telemetry module 47 awaits an ACK message from the receiving device, for example, the monitoring system 8 or a programmer 50 before the transmitter 55 is powered down. Thereby, the transmitter 55 is able to retransmit a communication package if the package for some reason was not received or if the data quality of the received data was too low.

Figure 4:
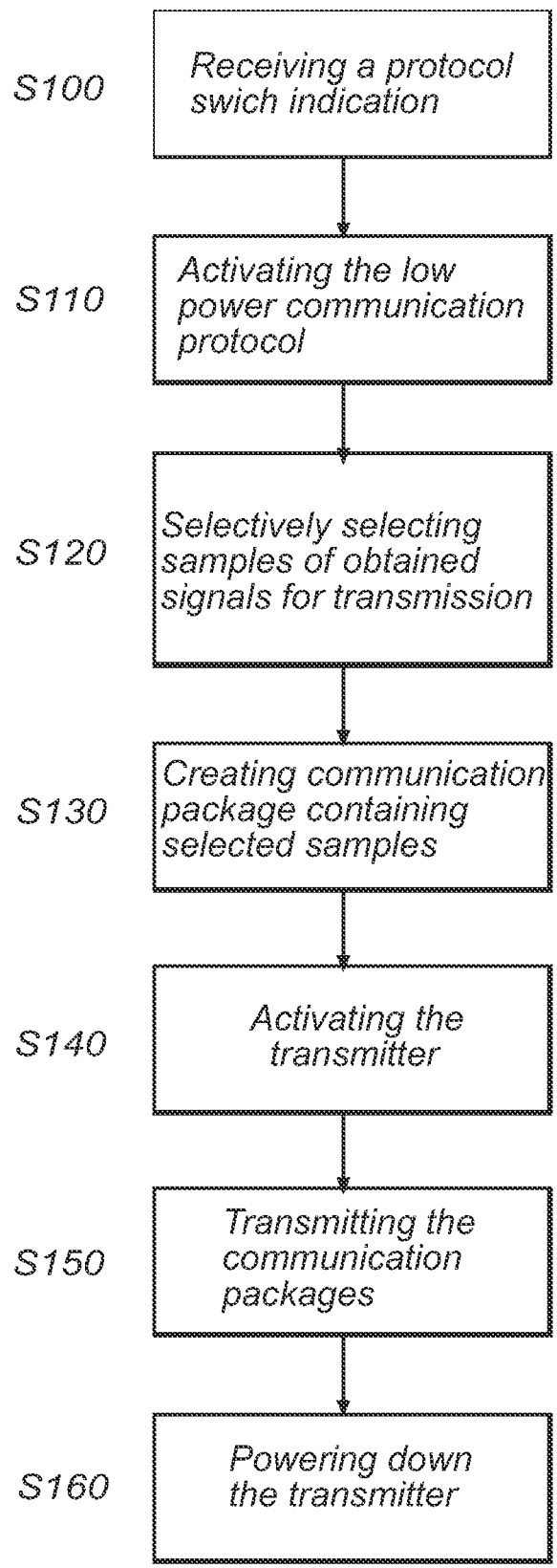
FIG. 4 schematically illustrates the principles of an embodiment of the method according to the present invention.

FIG. 4 is a flowchart describing the method according to the invention for enabling power efficient telemetric communication between an IMD 10 and external units 8, and 50 during long-term monitoring sessions, for example, during an MRI scan procedure.

First, at step S100, the protocol module 53 of the IMD receives a protocol switch indication informing the protocol module 53 that a protocol switch should be made, for example, from a RF default protocol to a low power protocol. This indication may be an indication of presence of an MRI field received from an MRI sensor 49 of the IMD or from an external device 8 or 50 (which may be sent automatically upon detection of the implanted device or manually by medical personnel attending at the MRI scan procedure). At receipt of the indication or the signal, the protocol module 53 activates or enters, at step S110, into the low power protocol for the telemetric communication with external devices 8 and/or 50 to enable remote monitoring of the patient as well as the functionality of the device during the long monitoring procedure at real time (with a time delay corresponding to the intermediate time period between the transmission bursts, which long monitoring procedure may be a MRI scan. When operative in the low power protocol, parts or samples of stored electrophysiological and/or hemodynamical signal waveforms are, at step S120, selected for telemetric transmission. As described above, the selected part may be selected samples of the IEGM signal, for example, every $4^{th}$ sample. In another embodiment, the sampling frequency is reduced such that the IEGMs are sampled with, for example, 64 Hz and the IEGMs obtained with reduced sampling frequency are stored. The selected parts in this embodiment are the stored IEGMs. According to both these embodiments, a reduced information content is achieved, which entails that a cardiac cycle is described or displayed using only a fraction of samples in comparison to the situation at, for example, a follow-up.

At step S130, communication packages having a predetermined length are created using the selected parts of the electrophysiological and/or hemodynamical signal waveforms. In a specific embodiment, where the sampling frequency is 64 Hz, the communication packages may have a length of about 25 ms.

At step S140, the telemetry module 47 is instructed to wake up or activate the transmitter 55. At every transmission session, for example, at every $3^{rd}$ or $4^{th}$ second the transmitter is activated and fully powered and during the intermediate intervals the transmitter is powered down or placed in the lowest possible operative capacity.

At step S150, the transmitter is instructed to transmit the communication packages. The information burst or transmission sessions are initiated at predetermined transmission intervals, for example, every $3^{rd}$ or $4^{th}$ second. Preferably, all selected data is transmitted in each burst, i.e. at each transmission session. That is, in one embodiment selected samples, for example, every $4^{th}$ sample of the stored IEGMs are transmitted in a communication package at each transmission session. In each communication package, the samples obtained during the period starting at the latest transmission interval. In another embodiment, the IEGMs are obtained with reduced sample frequency and are buffered and at transmission session the buffered samples are transmitted.

Subsequently, when the communication package has been sent and an ACK message has been received from the receiving device or system, at step S160, the telemetry module 47 is instructed to inactivate or power down the transmitter 55. During the intermediate intervals between the transmission sessions the transmitter 55 is powered down or placed in the lowest possible operative capacity. By this low power or low energy consumption protocol it is possible to significantly reduce the power consumption during long-term monitoring sessions such as under an MRI scan procedure. In a specific example, using 25 ms packages and information bursts every $3^{rd}$ second, the current consumption is about 0.1 mA and the energy consumption of the battery during an MRI scan procedure (about 3 hours long) is about 0.028% of the total battery capacity. If a normal RF communication protocol would be used during the MRI scan, the current consumption would be 2.8 mA and 0.76% of the battery capacity would be used.

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting.

The invention claimed is:

1. An implantable medical device comprising a telemetry module with a transmitter and a receiver and an input module being connectable to at least one electrode, the input module being adapted to obtain electrophysiological and/or hemodynamical signals from the heart via the at least one electrode at a predetermined sampling frequency, the device further comprising;
   a storage unit for storage of the obtained electrophysiological and/or hemodynamical signals;
   a protocol module adapted to, at receipt of a protocol switch indication, activate and use a low power protocol for communication between said device and external units, wherein said protocol module is adapted to:
   select parts of stored electrophysical and/or hemodynamical signal waveforms for telemetric transmission;
   create communication packages having a predetermined length using said selected parts of said electrophysiological and/or hemodynamical signal waveform;
   instruct said transmitter to transmit said communication packages at predetermined transmission intervals; and
   instruct said telemetry module to power down said transmitter during intermediate periods between said transmission intervals.

2. The implantable medical device according to claim 1, wherein said protocol module is adapted to, at said protocol switch indication, activate and use said low power protocol including:
   to instruct said input module to reduce the sampling frequency of the measurements of the electrophysiological and/or hemodynamical signals; and
   wherein the selected parts of the electrophysiological and/or hemodynamical signals correspond to the stored electrophysiological signals.

3. The implantable medical device according to claim 1, wherein said protocol module is adapted to, at said protocol switch indication, activate and use said low power protocol including:
   to select parts of stored electrophysiological and/or hemodynamical signal waveforms, wherein said parts are selected with predetermined intermediate time periods.

4. The implantable medical device according to claim 1, wherein said protocol switch indication is an indication of an MRI field.

5. The implantable medical device according to claim 4, wherein said indication of an MRI field is received from an external unit via said telemetry module.

6. The implantable medical device according to claim 4, further comprising an MRI field detector adapted to detect a presence of an external magnetic field having a magnetic field strength above a predetermined threshold as an MRI field and to indicate whether an MRI field is present, and to provide said indication of said presence of an MRI field to said protocol module.

7. The implantable medical device according to claim 6, wherein said MRI field detector is a Hall effect sensor.

8. The implantable medical device according to claim 1, wherein said protocol module is adapted to switch between said low power protocol and an RF default protocol depending on the protocol switch indication.

9. A method for an implantable medical device comprising a telemetry module with a transmitter and a receiver and an input module being connectable to at least one electrode, said input module being adapted to obtain electrophysiological and/or hemodynamical signals from the heart via said at least one electrode at a predetermined sampling frequency, said method comprising;
   storing of the obtained electrophysiological and/or hemodynamical signals;
   at receipt of an protocol switch indication, activating and using a low power protocol for communication between said device and external units, including:
   selecting parts of stored electrophysical and/or hemodynamical signal waveforms for telemetric transmission;
   creating communication packages having a predetermined length using said selected parts of said electrophysiological and/or hemodynamical signal waveform;
   instructing said transmitter to transmit said communication packages at predetermined transmission intervals; and
   instructing said telemetry module to power down said transmitter during intermediate periods between said transmission intervals.

10. The method according to claim 9, further comprising, at said protocol switch indication, activating and using said low power protocol including:
    instructing said input module to reduce the sampling frequency of the measurements of the electrophysiological and/or hemodynamical signals; and
    wherein the selected parts of the electrophysiological and/or hemodynamical signals correspond to the stored electrophysiological signals.

11. The method according to claim 9, further comprising, at said protocol switch indication, activating and using said low power protocol including:
    selecting parts of stored electrophysiological and/or hemodynamical signal waveforms, wherein said parts are selected with predetermined intermediate time periods.

12. The method according to claim 9, wherein said protocol switch indication is an indication of an MRI field.

13. The method according to claim 12, wherein said indication of an MRI field is received from an external unit via said telemetry module.

14. The method according to claim 12, further comprising detecting a presence of an external magnetic field having a magnetic field strength above a predetermined threshold as an MRI field, indicating whether a MRI field is present, and providing a signal indicating said presence of an MRI interference signal.

15. The method according to claim 14, wherein said MRI field detector is a Hall effect sensor.

16. The method according to claim 9, further comprising switching between said low power protocol and a RF default protocol depending on a protocol switch indication.

* * * * *